(12) United States Patent
Tegels et al.

(10) Patent No.: US 9,307,967 B2
(45) Date of Patent: Apr. 12, 2016

(54) LINKAGE DRIVEN COMPACTION DEVICE

(71) Applicant: St. Jude Medical Puerto Rico LLC, Caguas, PR (US)

(72) Inventors: Zachary J. Tegels, Minneapolis, MN (US); Steven Willard, Bloomington, MN (US)

(73) Assignee: ST. JUDE MEDICAL PUERTO RICO LLC, Caguas, PR (US)

(*) Notice: Subject to any disclaimer, the term of this patent is extended or adjusted under 35 U.S.C. 154(b) by 455 days.

(21) Appl. No.: 13/790,690

(22) Filed: Mar. 8, 2013

(65) Prior Publication Data
US 2014/0257372 A1   Sep. 11, 2014

(51) Int. Cl.
*A61B 17/00* (2006.01)

(52) U.S. Cl.
CPC ... *A61B 17/0057* (2013.01); *A61B 2017/00646* (2013.01); *A61B 2017/00654* (2013.01); *A61B 2017/00659* (2013.01); *A61B 2017/00672* (2013.01)

(58) Field of Classification Search
CPC ............... A61B 17/0057; A61B 19/30; A61B 2017/00637; A61B 17/00654; A61B 2017/00646; A61B 2017/00659
See application file for complete search history.

(56) References Cited

U.S. PATENT DOCUMENTS

| | | | |
|---|---|---|---|
| 6,045,569 A | 4/2000 | Kensey et al. | |
| 6,090,130 A | 7/2000 | Nash et al. | |
| 7,597,705 B2 | 10/2009 | Forsberg et al. | |
| 7,618,436 B2 | 11/2009 | Forsberg | |
| 7,749,248 B2 | 7/2010 | White et al. | |
| 7,837,705 B2 | 11/2010 | White et al. | |
| 7,931,670 B2 | 4/2011 | Fiehler et al. | |
| 2005/0085851 A1* | 4/2005 | Fiehler ............... | A61B 17/0057 606/213 |

* cited by examiner

*Primary Examiner* — Ashley Fishback
(74) *Attorney, Agent, or Firm* — Holland & Hart

(57) ABSTRACT

Methods and apparatus are disclosed for sealing a puncture or incision formed percutaneously in tissue separating two internal portions of the body of a living being with an anchor, a sealing plug and a filament connecting the anchor and sealing plug. The methods and apparatus provide for a compaction mechanism that is expandable and tamps the sealing plug into place.

17 Claims, 13 Drawing Sheets

LINKAGE DRIVEN COMPACTION DEVICE

FIELD OF TECHNOLOGY

This disclosure relates generally to medical devices and more particularly to tools for sealing punctures or incisions in a tissue wall.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,090,130; 6,045,569; 7,597,705; 7,618,436, 7,749,248; 7,931,670; 7,837,705; and related patents and patent applications, all of which are hereby incorporated by reference.

Typical closure tools or devices such as the ones described in the above-mentioned patents place a sealing plug at the tissue puncture site. Successful deployment of the sealing plug requires that it be ejected from within a device sheath into the incision or puncture tract and tamped down to an outer surface of the tissue puncture using a tamping tube (also called a compaction tube). In an automatic tamping system, the closure tool can have an automatic tamping mechanism for automatically tamping the sealing plug within the incision or puncture tract toward the outer surface of the tissue puncture. The closure tool can have a tamping tube disposed adjacent to the sealing plug, such that the tamping tube is driven by the automatic tamping mechanism to tamp the sealing plug into the desired placement.

The automatic tamping mechanism can take up linear space, especially if the automatic tamping mechanism used to tamp the sealing plug is a linear rack. The linear rack can be stored in the handle, which can result in a long handle design, to accommodate the linear rack. Alternatively, the automatic tamping mechanism can be a coilable rack. Such a coilable rack can be coiled in the handle and, as the coilable rack approaches the tamping tube or compaction tube, the rack straightens and becomes linear. The coilable rack may not have the column strength that the linear rack may have. However, the ability of the rack to coil can result in a smaller, more compact handle. Nevertheless, there is a need for improving the automatic tamping mechanism, where the mechanism can provide the columnar tamping strength for disposing a sealing plug at the external wall of a puncture.

SUMMARY

In one of the many possible embodiments, the present disclosure provides an automatic compaction mechanism or an automatic tamping mechanism for tamping a sealing plug within an incision or puncture tract, towards the outer surface of a vessel puncture or tissue puncture, where the automatic compaction mechanism is adapted to extend its length and provide the compaction strength to tamp a sealing plug into place. It should be noted that the terms "compaction" and "tamping" are used interchangeably and refer to the same action of placing a sealing plug in the desired position in a puncture tract. Further, the term "compaction mechanism" and "tamping mechanism" refer to the same component of the tissue puncture closure tool. The term "compaction member" may refer to a "compaction tube" or other such similar device, and the term "tamping member" may refer to a "tamping tube". The term "compaction tube" may be used interchangeably with the term "tamping tube". In one aspect, the compaction mechanism of the present disclosure can be used in a tissue puncture closure tool where the compaction mechanism can be engaged with the compaction tube and automatically tamp the sealing plug into the desired position in the puncture tract.

According to one aspect of the disclosure, a compaction mechanism can comprise a system of linkages wherein the mechanism formed by the system of linkages can be engaged with a compaction member, for example, a compaction tube, and can tamp a sealing plug to a desired position.

In another aspect of the disclosure, a compaction mechanism can comprise a system of linkages, wherein the quantity of linkages can be varied, such that the amount of linear travel that the compaction device can undergo can be varied.

In yet another aspect of the disclosure, the compaction mechanism can comprise a system of linkages, where the linkages are connected to each other, and are also connected to a fixed point. A number of linkages can be disposed to one side of the fixed point and a number of linkages can be disposed to another side of the fixed point, such that the number of linkages on one side of the fixed point affects the amount of linear travel of the linkage system and, thus, the compaction device, as the compaction device urges the sealing plug into a desired position within a puncture tract.

In another aspect of the disclosure, the compaction mechanism can comprise a single linkage which can expand horizontally, as the linkage collapses vertically. The single linkage can be coupled to a compaction device, and the motion of the linkage expanding horizontally and collapsing vertically can drive the compaction device towards a sealing plug, and urge the sealing plug into a desired position within a puncture tract.

In another aspect of the disclosure, a compaction member drive the compaction device at a rate at least twice the rate of outer arm linkages, providing the tamping strength to tamp a sealing plug into a desired position within a puncture tract. Further, the compaction mechanism may require less linear resting space as compared to a linear rack, yet may travel a similar longitudinal distance.

In yet another aspect of the disclosure, a tissue puncture closure tool is disclosed wherein the tissue puncture closure tool can comprise one of the compaction mechanisms described above.

One skilled in the art would understand that the various aspects of the present disclosure described above can be combined and intermixed into various other arrangements and combinations, to achieve the desired compaction of the sealing plug in the tissue puncture.

According to another aspect of the disclosure, there is disclosed a tissue puncture closure tool for partial insertion into and sealing of an internal tissue wall puncture. The tissue puncture closure tool includes a filament extending from a first end of the closure tool to a second end of the closure tool, an anchor for insertion through the tissue wall puncture attached to the filament at the second end of the closure tool, a sealing plug slidingly coupled to the filament adjacent to the anchor, and a compaction device disposed proximally adjacent to the sealing plug for advancing the sealing plug toward the anchor. The compaction device can be a tubular member, for example, a compaction tube or a tamping tube. The compaction device can be urged toward the sealing plug and anchor by a compaction mechanism, the compaction mechanism being in the form of, for example, a series of interconnected linkages which extend and contract in a scissor-like motion. Alternatively, the compaction mechanism can comprise a single linkage which collapses in one direction, for example, vertically, and extends in a perpendicular direction, for example, horizontally, to drive a compaction member. The tissue puncture closure tool can include a spool or a roller such that the filament or suture winds along the spool or roller, and tension on the filament or suture affects the extension of the compaction mechanism, which in turn effects the compaction of the sealing plug within a tissue puncture tract, by way of the compaction device.

The above summary of the various representative embodiments of the disclosure is not intended to describe each illustrated embodiment or every implementation of the disclosure. Rather, the embodiments are chosen and described to that others skilled in the art may appreciate and understand the principles and practices of the disclosure. The figures in the detailed description that follows more particularly exemplify these embodiments.

BRIEF DESCRIPTION OF THE DRAWINGS

These as well as other objects and advantages of this disclosure will be more completely understood and appreciated by referring to the following more detailed description of the exemplary embodiments of the disclosure in conjunction with the accompanying drawings of which.

Figure 1:
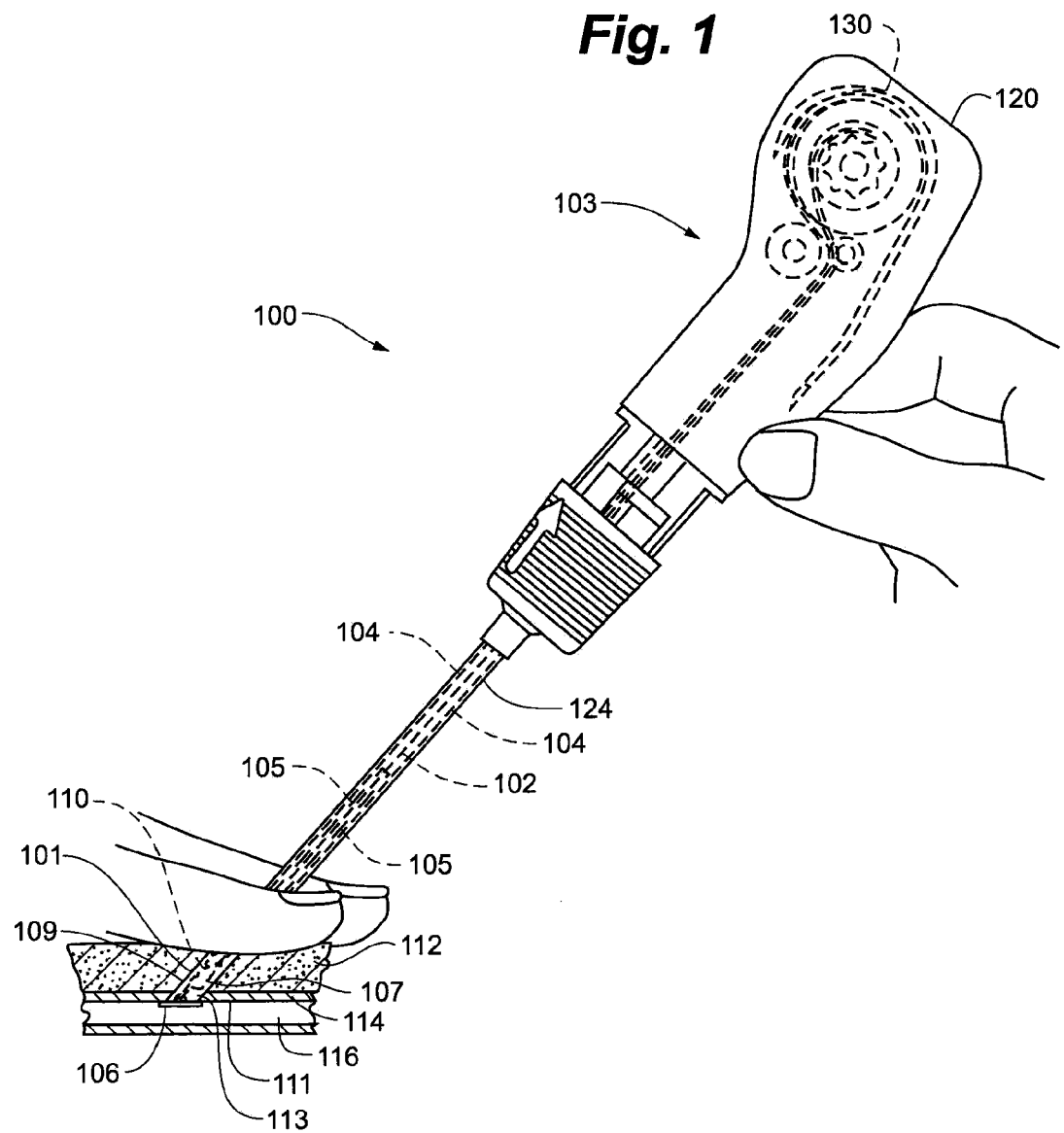
FIG. 1 is a side view of a tissue puncture closure tool.

The figures are not necessarily presented as drawn to scale.

DETAILED DESCRIPTION

As mentioned above, vascular procedures are conducted throughout the world and require access to an artery through a puncture. Most often, the artery is a femoral artery. To close the puncture following completion of the procedure, many times a closure tool is used to sandwich the puncture between an anchor and a sealing plug. The closure tool can also be used to close other tissue punctures, punctures other than a puncture accessing a blood vessel, but punctures that access some other cavity or lumen. However, sometimes the sealing plug is not properly seated against an exterior situs of the tissue puncture, for example, of the arteriotomy. If the plug does not seat against the arteriotomy, there is a potential for prolonged bleeding. Further, the closure tool may not include a tamping device or a compaction mechanism that provides the needed column strength and tamping necessary to dispose the sealing plug in the desired position within the puncture tract, adjacent the tissue puncture. In addition, the closure tool handle may be somewhat uncomfortable or unwieldy to use, especially for someone with smaller hands, and yet a large handle may be required to house a tamping device and/or a compaction mechanism. The present disclosure describes methods and apparatus to reduce or eliminate misplacement of the sealing plug, as well as providing for a substantially compact tissue puncture closure tool. While the vascular instruments shown and described below include insertion sheaths and puncture sealing devices, the application of principles described herein is not limited to the specific devices shown. The principles described herein may be used with any vascular closure, tissue closure, or similar device.

As used in this specification and the appended claims, the term "tamp" or "tamping" is used broadly to mean packing down by one or a succession of blows or taps or smooth, steady pressure. A "tamping device" or "tamping member" is used broadly to mean any elongated device or series of devices, including any intermediate components, used alone or in combination to tamp something else directly or indirectly, for example, a tamping tube. The term "compaction device" or "compaction member" is used interchangeably with the term "tamping member" and the term "compaction tube" is used interchangeably with the term "tamping tube". Similarly, the term "tamping mechanism" is used interchangeably with the term "compaction mechanism". "Engage" and "engageable" are also used broadly to mean interlock, mesh, or contact between two devices. A "spool" is a cylinder, spindle, or other device on which or along which something else, for example, a suture, thread or filament, is at least partially wound, however the spool can also act as a guide. The term "roller" can be used interchangeably with the term "spool". A "lumen" refers to any open space or cavity in a bodily organ or device, especially in a blood vessel. The term "suture" is used interchangeably with the terms "thread" and "filament". "Automatic" means no action or intervention is required by a human operator. "Transduce" means to convert a force or other input energy in one form into output energy or forces of another form or direction. "Gradually" means advancing or progressing by regular or continuous degrees, or absent any abrupt changes. "Sudden" refers to a rapid, abrupt, or quick change. The words "including" and "having," as used in the specification, including the claims, have the same meaning as the word "comprising."

Figure 2:
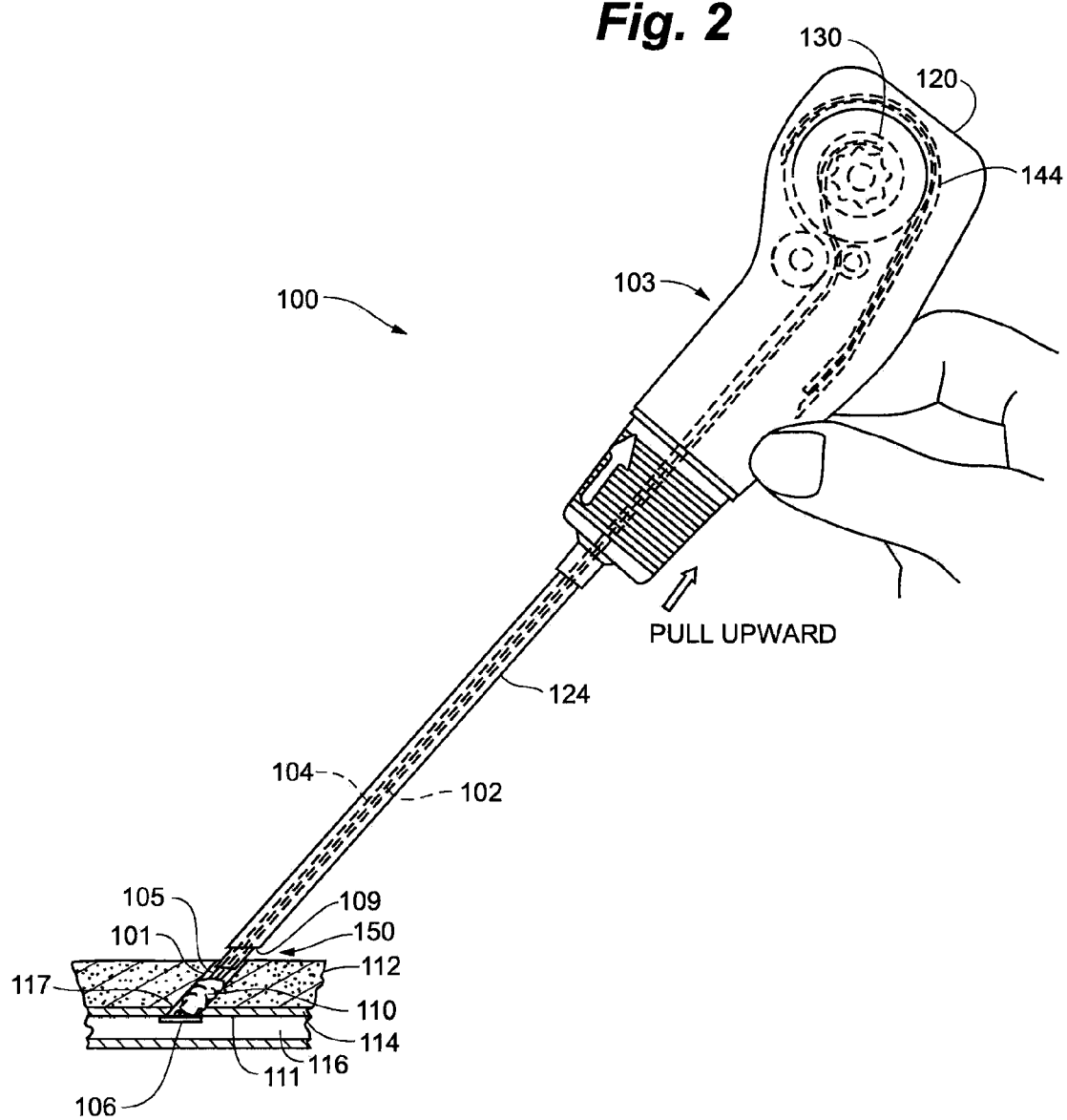
FIG. 2 is a side view of the tissue puncture closure tool of FIG. 1 inserted through an insertion sheath, with the sealing plug deployed.

Referring now to the drawings, and in particular to FIGS. 1-2, a vascular puncture closure tool 100 is shown according to the prior art. The tissue puncture closure tool 100 includes a first or proximal end 103 and a second or distal end 150. A carrier tube 104 extends from the proximal end 103 to the distal end 150 and includes an outlet 113. The carrier tube 104 may be made of plastic or other material and is designed for insertion through a sheath 124 which is designed for insertion through a percutaneous incision 101 in a tissue layer 112 and into a lumen 116. As shown in FIG. 1, the lumen 116 defines an interior portion of a femoral artery 114, but the lumen could define another tissue or organ interior wall.

The distal end 107 of the carrier tube 104 includes a sealing plug 110 housed therein, until the sealing plug 110 is deployed, and an anchor 106 is disposed adjacent the distal end 107 of the carrier tube 104. The anchor 106 is an elongated, stiff, low-profile member preferably made of a biologically resorbable polymer. The sealing plug 110 is formed of a compressible sponge, pad, or foam, made of a hemostatic biologically resorbable material such as collagen, and may be configured in any shape so as to seal the tissue puncture 101.

The sealing plug 110 and anchor 106 are connected to one another by a suture, thread, or filament 102 that is also biologically resorbable. The suture 102 extends distally from the first end 103 of the closure tool 100 through the carrier tube 104. The suture 102 can be threaded through the sealing plug 110, then through a hole in the anchor 106 and proximally back through the carrier tube 104 to the sealing plug 110. The suture 102 is preferably threaded through a perforation or series of perforations in the sealing plug 110. The suture 102 can also be threaded around itself to form a slip-knot, proximate of the sealing plug 110. The suture 102 thus can connect the anchor 106 and the sealing plug 110 in a pulley-like arrangement that serves to cinch the anchor 106 and the sealing plug 110 together when the carrier tube 104 is pulled away from the anchor 106 and the sealing plug 110, sandwiching and locking the anchor 106 and plug 110 together and thereby sealing the tissue puncture 101.

The carrier tube 104 also includes a compaction device, for example, a tamping tube or compaction tube 105, for tamping the sealing plug 110 along the suture 102 and against the anchor 106. The compaction tube 105 is shown located within the carrier tube 104 and proximal of the sealing plug 110. The compaction tube 105 can be an elongated tubular member that can be rigid or flexible and formed of any suitable material. The suture 102 extends through the compaction tube 105 but is not directly connected thereto. Accordingly, the suture 102 and compaction tube 105 are free to slide past one another. Referring to the embodiment of FIG. 1, the suture 102 extends beyond a proximal end of the compaction tube 105 and attaches to an automatic driving mechanism 130 located within a housing 120 at the first end 103 of the closure tool 100.

In practice, the carrier tube 104 of the closure tool 100 (containing the suture 102 and sealing plug 110) can be inserted into an insertion sheath 124, which is already inserted within the artery 114. As the closure tool 100 and the associated closure elements are inserted into the insertion sheath 124, the anchor 106 passes through and out of a distal end 109 of the insertion sheath 124 and is inserted into the artery or other tissue lumen 116. The tissue puncture closure tool 100 can then be withdrawn from the insertion sheath 124 until the anchor 106 catches on the distal end 109 of the insertion sheath 124 and rotates to the position shown in FIG. 1. When resistance to further retraction of the closure tool 100 is felt by an operator, the closure tool 100 and the insertion sheath 124 can be withdrawn together, causing the anchor 106 to anchor itself within the artery 114 against the artery wall 111. With the anchor 106 anchored within the artery 114 at the puncture site 117, further retraction of the closure tool 100 and insertion sheath 124 causes the sealing plug 110 to withdraw from the distal end 107 of the carrier tube 104, thereby depositing the plug 110 within the incision or puncture tract 101.

The tissue puncture closure tool 100 automatically tamps the sealing plug 110 into place. The automatic driving mechanism 130 drives, via a rack or compaction tube driver 144, the compaction tube 105 toward the sealing plug 110 automatically upon withdrawal of the closure tool 100 from the puncture tract, tamping the plug 110 toward the anchor 106 as shown in FIG. 2. The rack or compaction tube driver 144 can be coilable or can be a linear rack. The sealing plug 110 is tamped while the carrier tube 104 is still arranged adjacent to the puncture 101 in the femoral artery 114, reducing or eliminating any gaps that may otherwise occur between the sealing plug 110 and the puncture 101 in the femoral artery 114.

In addition, by placing tension on or pulling the suture 102 away (proximally) from the puncture tract 101, the suture 102 cinches and locks (with a slip knot or the like) together the anchor 106 and the sealing plug 110, sandwiching the artery wall 111 between the anchor 106 and sealing plug 110. The force exerted by the compaction tube 105 and the cinching together of the anchor 106 and sealing plug 110 by the suture 102 also causes the sealing plug 110 to deform radially outward within the puncture tract and function as an anchor on the proximal side of the tissue puncture site 117.

It is understood that the sealing of a puncture in an artery or other blood vessel wall is given as an example, and that the closure device can be used for sealing other tissue punctures, with the anchor sealing the interior surface of the tissue lumen and the sealing plug providing additional hemostasis in the puncture tract. Applications of closure tools, including those implementing principles described herein, include closure of a percutaneous puncture or incision in tissue separating two internal portions of a living body, such as punctures or incisions in blood vessels, ducts or lumens, gall bladders, livers, hearts, etc.

As noted above, once the anchor 106 is anchored within the artery 116 at the puncture site, further retraction of the closure tool 100 and insertion sheath 124 causes the sealing plug 110 to withdraw from the distal end 107 of the carrier tube 104 and to be tamped by the tamping tube 105 into position at the outer surface of the wall of the puncture site 117. A linear rack or a coilable rack 144 drives the tamping tube 105 such that the tamping tube 105 tamps the sealing plug 110 into place. However, the length of the linear rack can affect the size of the handle since the housing 120 of the handle accommodates the length of the rack. Further, the handle houses the spooled length of suture required to extend between the anchor 106 and the proximal end of the closure tool, as the closure tool is removed from the incision 101. It remains important to position the sealing plug 110 properly; otherwise poor positioning could result in poor sealing of the tissue puncture or incision 101, leading to body fluid leakage. Therefore, there is a need for a closure tool that provides secure positioning of the sealing plug as well as a comfortable-to-use handle, and is economical.

Figure 3:
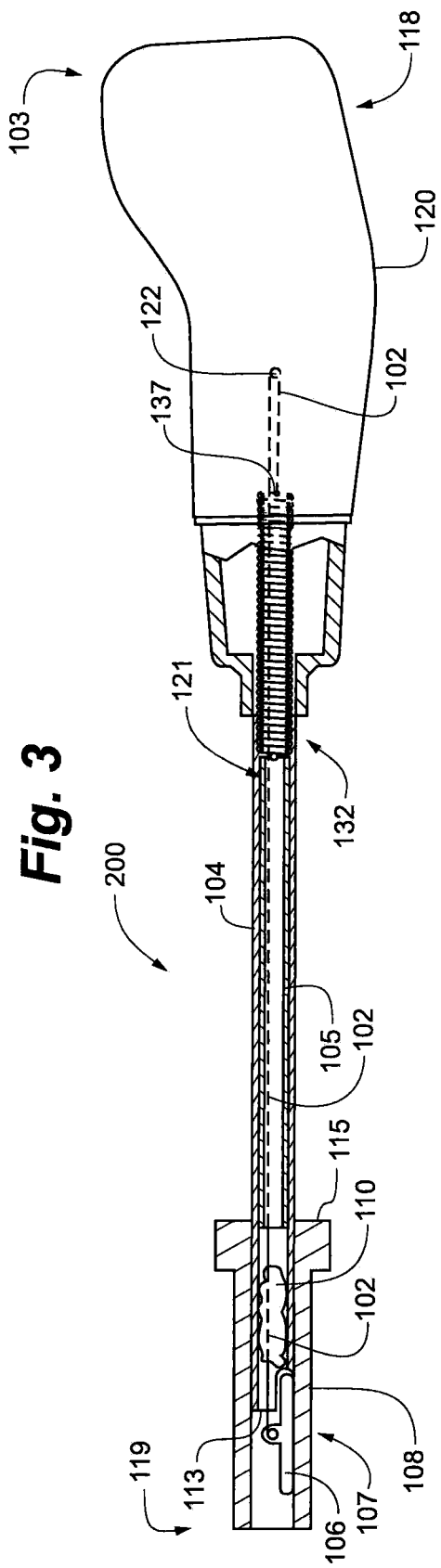
FIG. 3 is a side view of an embodiment of a tissue puncture closure tool of the present disclosure.

Referring to FIGS. 3-13, there are shown examples of tissue puncture closure tools usable in sealing a puncture or incision 101. The devices and methods of the disclosure can be used for sealing various types of punctures and/or incisions, however, sealing a percutaneous puncture used to access the femoral artery is given as just a general example of such use. Referring now to FIG. 3, there is shown a tissue puncture closure tool 200. Where components are similar to components of the tissue puncture closure tool 100 described above, similar numeric identifiers will be used. The tissue puncture closure tool 200 includes a proximal end 103 and a second or distal end 119. A carrier tube 104 extends substantially from the proximal end 103 to the distal end 119 of the closure tool 200 and includes an outlet 113. As noted above, the carrier tube 104 is designed for insertion through a sheath 124 which is designed for insertion through a percutaneous incision 101 in a tissue layer and into a lumen 116. The distal end 119 of the closure tool 200 houses an anchor 106 and a sealing plug 110, with the sealing plug 110 disposed within the carrier tube 104. Here, too, the anchor 106 can be an elongated, stiff, low-profile member preferably made of a biologically resorbable polymer, however other shapes, for example, oval or round, are contemplated. Similarly, the sealing plug 110 is formed of a compressible material, for example, a sponge, pad, or foam, made of a hemostatic biologically resorbable material such as collagen, and may be configured in any shape so as to seal a tissue puncture.

The sealing plug 110 and anchor 106 are connected to one another by a suture, thread, or filament 102 that is also biologically resorbable. The suture 102 extends distally from the handle 118 of the closure tool 200 through the carrier tube 104. The suture 102 can be threaded through the sealing plug 110, then through a hole in the anchor 106 and proximally back through the carrier tube 104 to the sealing plug 110. The suture 102 is preferably threaded through a perforation or series of perforations in the sealing plug 110. The suture 102 can also be threaded around itself to form a slip-type knot at the proximal side of the sealing plug 110. The suture 102 thus can connect the anchor 106 and the sealing plug 110 in a pulley-like arrangement that serves to cinch the anchor 106 and the sealing plug 110 together when the carrier tube 104 is pulled away from the anchor 106 and the sealing plug 110, sandwiching and locking the anchor 106 and plug 110 together and thereby sealing a tissue puncture 101.

The carrier tube 104 also houses a compaction device, for example, a tubular member. The tubular member can be a tamping tube or compaction tube 105, or other compaction device, for tamping the sealing plug 110 along the suture 102 and distally toward the anchor 106. The compaction tube 105 is shown located within the carrier tube 104 and proximal of the sealing plug 110. The compaction tube 105 can be an elongated tubular member that can be rigid or flexible and formed of any suitable material. The suture 102 can extend through the compaction tube 105 but is not directly connected thereto. Accordingly, the suture 102 and compaction tube 105 are free to slide past one another. Referring to the embodiment of FIG. 3, the suture 102 can extend beyond a proximal end of the carrier tube 104, round a spindle, roller, spool guide 122, or the like, and can be coupled to an automatic compaction mechanism 132, the automatic compaction mechanism 132 can be disposed partially within the carrier tube 104 and partially disposed within the handle housing 120. An end of the suture 102 can be coupled to the proximal end of the automatic compaction mechanism 132 and the other end of the suture 102 can form a slip-type knot at the proximate side of the sealing plug 110, as described above.

Figure 6:
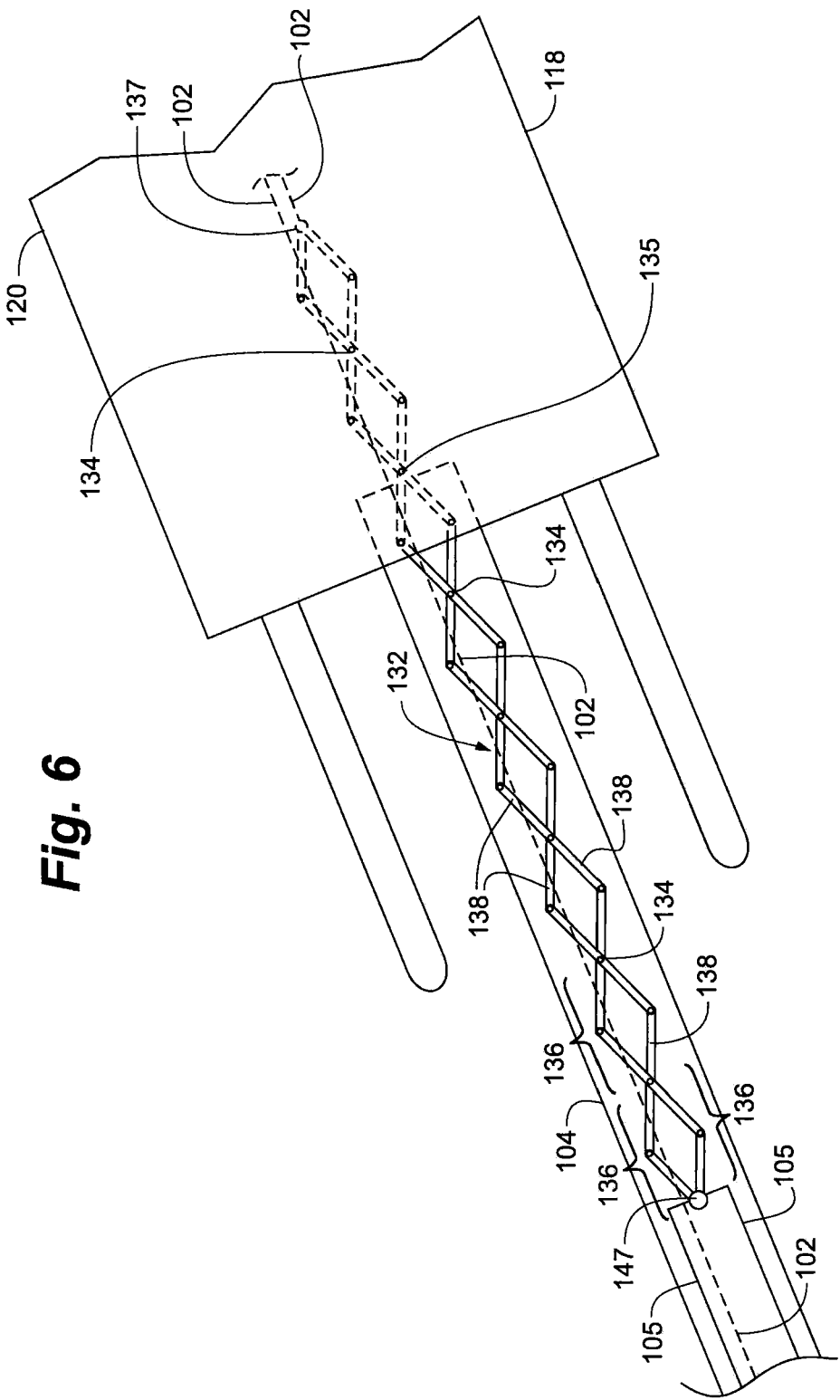
FIG. 6 is an enlargement of a section of the compaction mechanism.
Figure 10:
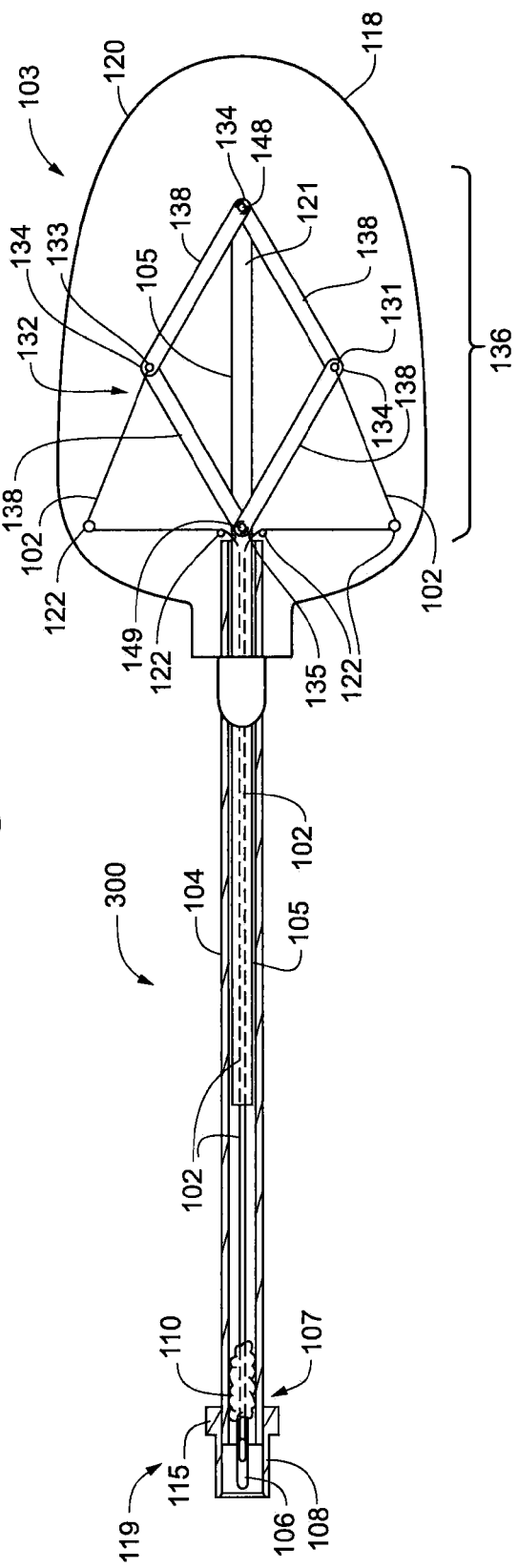
FIG. 10 is a top view of a tissue puncture closure tool of the present disclosure.

In one embodiment, as shown in FIG. 6, the automatic compaction mechanism 132 can comprise a series of linkages 136, each linkage 136 comprising a plurality of arms 138. In the embodiment shown in FIG. 6, each linkage 136 comprises four arms 138, where the arms 138 are interconnected by way of pivot points 134. The arms 138 can be fastened to each other at the pivot points by way of a fastener, grommet, or the like, where the created joint is movable and bendable. However, alternative configurations are contemplated as shown in FIG. 10. Each linkage 136, when the arms 138 are flexed, can form a diamond-shape. The linkages 136 can be connected in series, as one linkage 136 shares a pivot point 134 with an adjacent linkage 136. A pivot point 134 disposed in a proximal portion in the series of linkages 136 can be coupled to the handle housing 120, establishing a fixed pivot point 135. The proximate-most pivot point 137 in the series of linkages 136 can be coupled to the suture 102. The suture 102 coupled to the proximate-most pivot point 137 can travel proximally, pass over a spool or roller guide 122, preferably a grooved spool or roller guide 122, and change direction, travelling distally towards the anchor 106. The suture 102 can pass from the spool 122, traveling distally, into the carrier tube 104, pass through the tamping tube 105, through the sealing plug 110, through an aperture in the anchor 106, back through the sealing plug 110, and form a slip-type knot on the proximal side of the sealing plug 110. The spool or roller guide 122 can be directly or indirectly coupled to the handle housing 120.

Figure 7:
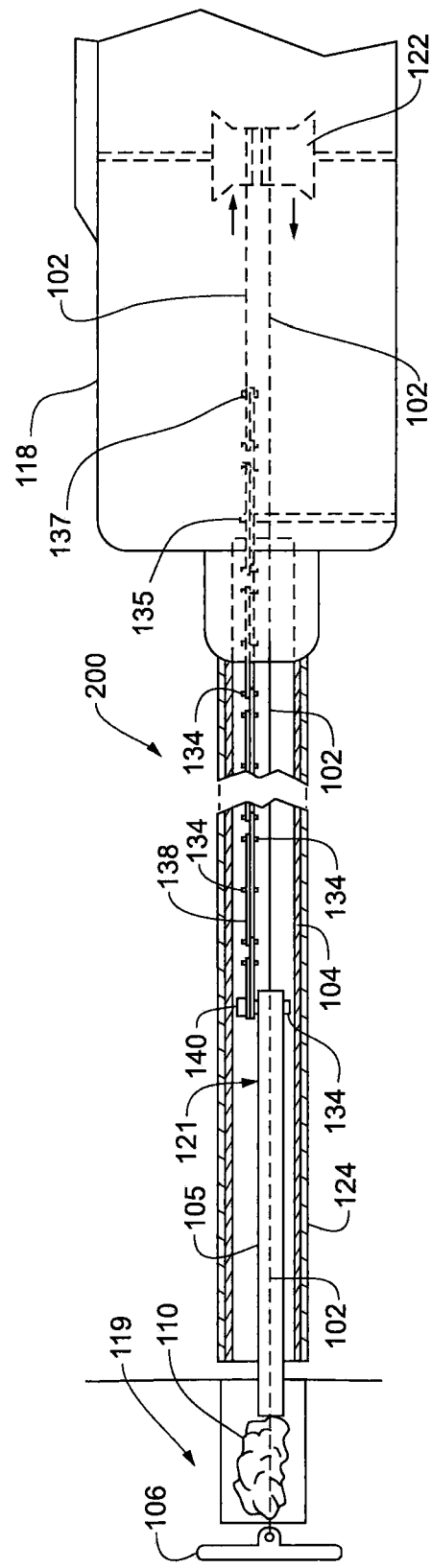
FIG. 7 is a side view of the tissue puncture closure tool shown in FIG. 3.

Referring to FIG. 7, there is shown a side view of a portion of the tissue puncture closure device 200. The series of linkages 136 are shown in profile, with the pivot points 134 linking the arms 138 into a continuous compaction mechanism. The fixed pivot point 135 can be coupled to the handle housing 120, and one end of the suture 102 can be coupled to the proximate-most pivot point 137. The suture 102 can travel proximally, traverse a spool or roller guide 122, change direction, and travel distally towards the anchor. As shown in FIG. 7, the suture 102 can pass into the carrier tube 104, continue through the tamping tube 105, through the sealing plug 110, attach to the anchor 106, pass back through the sealing plug 110, and form a slip-type knot on the proximal side of the sealing plug 110. The suture 102 does not impede the motion of the compaction mechanism 132 as the suture 102 passes through and within the carrier tube 104.

In operation, the tissue puncture closure tool 200 can be inserted into a sheath 124 that has already been inserted into a puncture tract 101. The bypass tube 108, which holds the anchor 106 in place adjacent the carrier tube 104, bears against a surface of the sheath 124. The bypass tube 108 (FIG. 3) includes an oversized head 115 that prevents the bypass tube 108 from passing through an internal passage of the insertion sheath 124. Therefore, as the puncture closure tool 200 is inserted into the insertion sheath 124, the oversized head 115 bears against a surface of the insertion sheath 124. Further insertion of the puncture closure tool 200 results in sliding movement between the carrier tube 104 and the bypass tube 108, releasing the anchor 106 from the bypass tube 108. However, the anchor 106 remains in the flush arrangement shown in FIG. 3 following release from the bypass tube 108 as the insertion sheath 124 continues to limit anchor 106 movement.

The insertion sheath 124 includes a monofold at a second or distal end of the insertion sheath 124. The monofold acts as a one-way valve to the anchor 106. The monofold is a plastic deformation in a portion of the insertion sheath 124 that elastically flexes as the anchor 106 is pushed out through the distal end of the sheath 124. Typically, after the anchor 106 passes through the distal end of the insertion sheath 124 and enters the artery lumen 116, the anchor 106 is no longer constrained to the flush arrangement with respect to the carrier tube 104 and the anchor 106 deploys, can catch on the distal end of the insertion sheath 124, and rotates to the position shown in, for example, FIG. 4 or FIG. 7.

Figure 5:
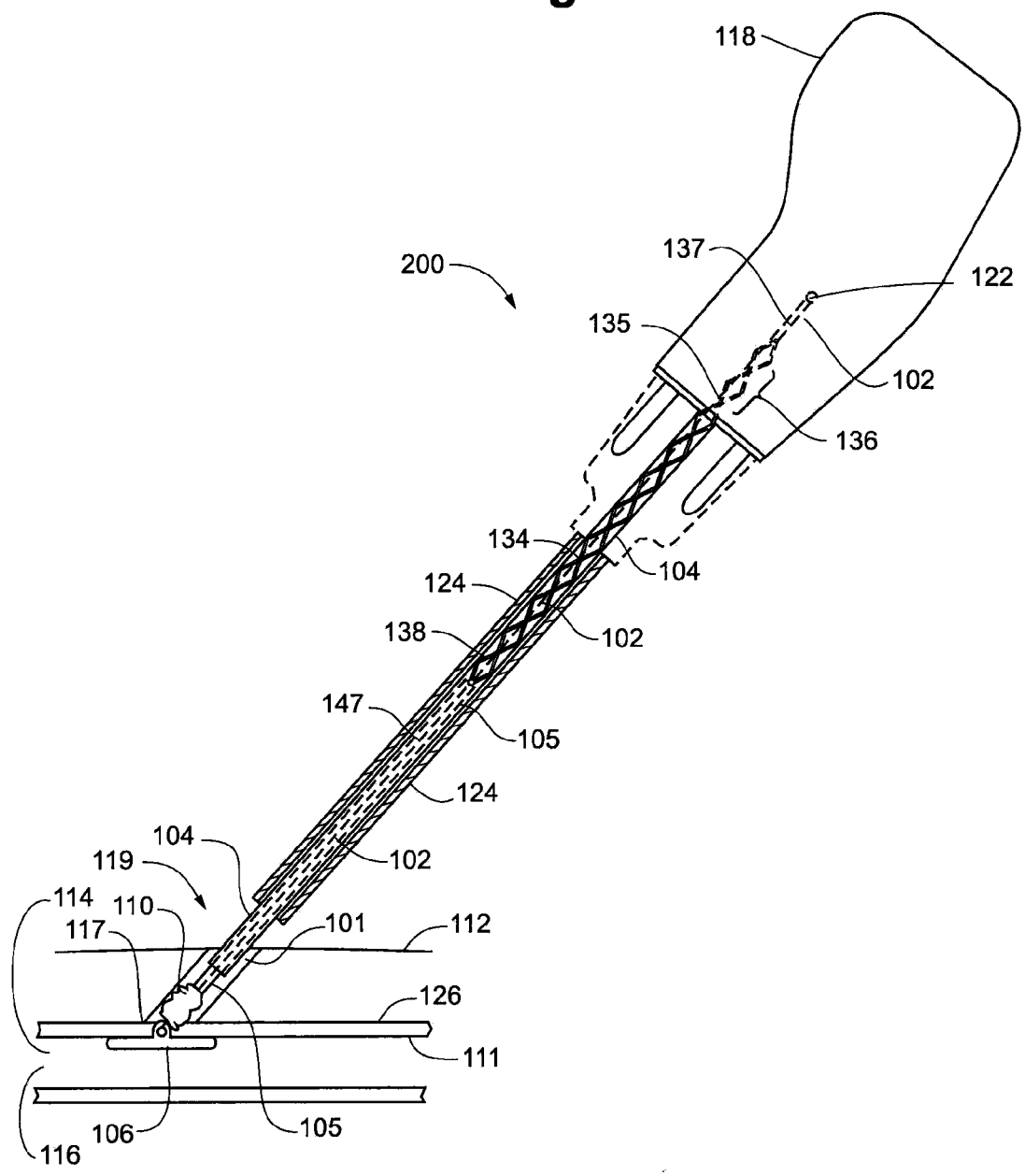
FIG. 5 is a side view of the tissue puncture closure tool shown in FIG. 3 with a substantially extended compaction mechanism.

The closure tool 200 can begin to be retracted, which can further position the anchor 106 in proper position against the inner wall of the lumen, for example, against the inner wall 111 of the artery. When resistance to further retraction of the closure tool 200 is felt by an operator, the closure tool 200 and the insertion sheath can be withdrawn together, causing the anchor 106 to anchor itself within the artery 114 against the artery wall 111. With the anchor 106 anchored within the artery 114 at the puncture site 117, further retraction of the closure tool 200 and insertion sheath 124 causes the sealing plug 110 to deploy from the distal end 107 of the carrier tube 104, thereby depositing the plug within the incision or puncture tract 101. With some retraction of the closure tool 200 and sheath 124, tension on the suture 102 increases, and the compaction mechanism 132 begins to expand, driving the tamping tube 105 distally in the carrier tube 104, and automatically tamping the seal plug 110 into place within the incision 101 (FIG. 5). The sealing plug 110 is tamped while the carrier tube 104 is still arranged adjacent to the puncture 117 in the artery 114, reducing or eliminating any gaps that may otherwise occur between the sealing plug 110 and the puncture 117 in the artery 114.

Figure 4:
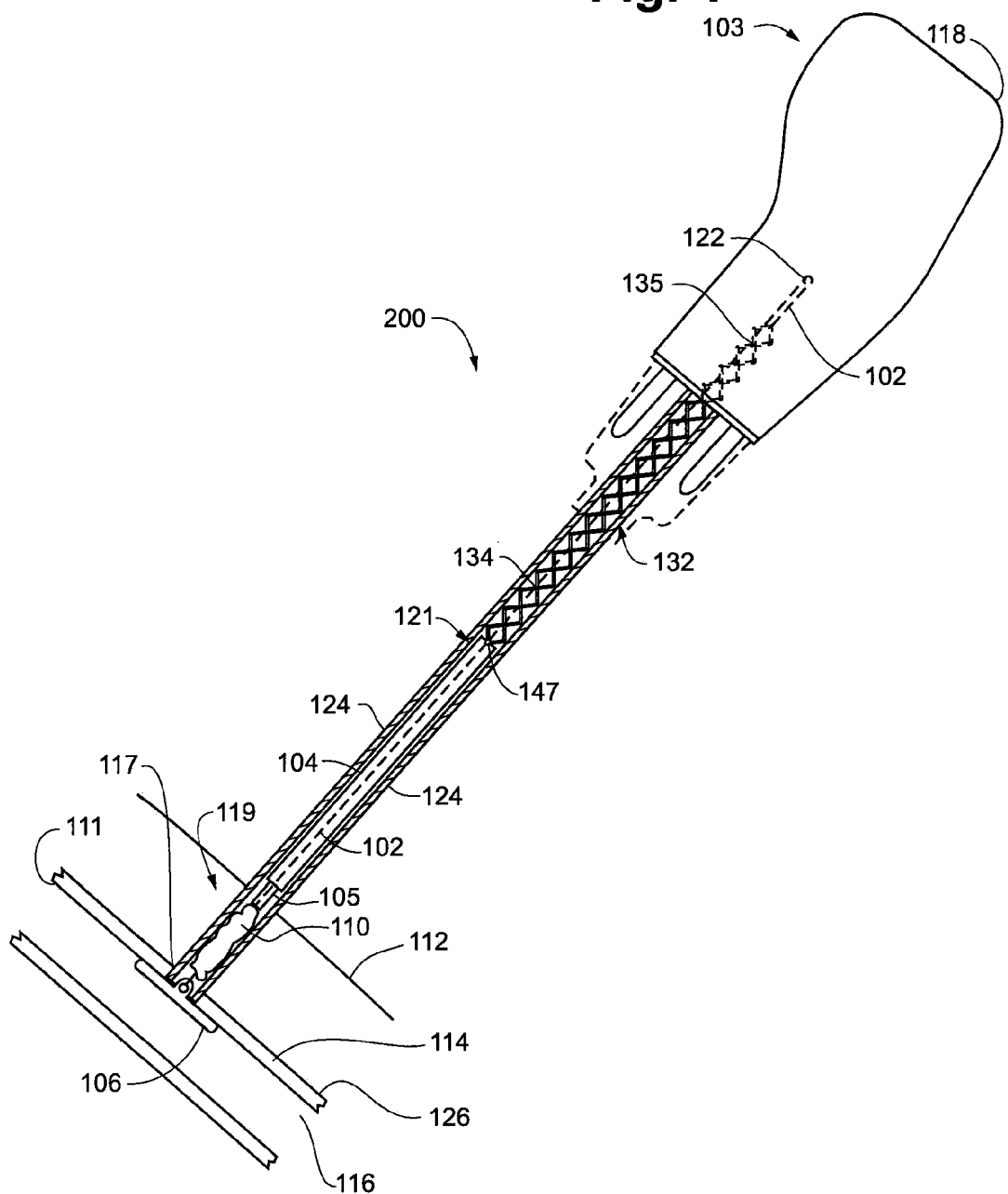
FIG. 4 is a side view of the tissue puncture closure tool shown in FIG. 3 with an extending compaction mechanism.

As noted above, the compaction mechanism 132 can begin to expand as the carrier tube 104 and sheath 124 are withdrawn together from the incision 101. FIG. 3 shows the compaction mechanism 132 in a collapsed or "at rest" configuration, prior to the deployment of the anchor 106. The arms 138 are folded together or collapsed, with similarly positioned arms 138 arranged substantially parallel one to another. The series of arms 138 can be somewhat slanted, in the collapsed state, at an angle of between about 5 degrees and 15 degrees. Once the anchor 106 catches on the distal end 107 of the insertion sheath 124 and rotates to a position parallel with the artery or tissue wall, flush against the puncture, thereby covering the puncture of the inner surface of the tissue or artery wall 111, the insertion sheath 124 and the closure tool 200 can be further withdrawn together. The action of further withdrawing the insertion sheath 124 and closure tool 200 together can cause the sealing plug 110 to deploy from the distal end 107 of the carrier tube 104, depositing the plug 110 within the incision or puncture tract 101. The motion of withdrawing the insertion sheath 124 and the closure tool 200 can result in the tension on the suture 102 end that is coupled to the anchor 106 and sealing plug 110 to increase, thus in turn resulting in the suture 102 portion that is disposed around the spool or roller guide 122 to transfer that tension to the portion of the suture 102 that is coupled to the proximate-most or end pivot point 137 of the compaction mechanism 132. The tension on the suture 102 can result in the end pivot point 137 traveling proximally, and thus expanding the arms 138 of the linkage 136, such that the linkage 136 expands proximally. However, due to the fixed pivot point 135, the linkages 136 that are disposed distal of the fixed pivot point 135 expand distally, towards the anchor 106 and sealing plug 110. With the distal-most linkage 136 coupled to the proximal end portion 121 of the compaction tube 105, the expanding linkages 136 distal of the fixed pivot point 135 urge the compaction tube 105 in a distal direction, toward the sealing plug 110 (as shown in FIG. 4). As the insertion sheath 124 and closure tool 200 continue to be withdrawn together, the tension on the suture 102 continues to result in the proximate linkage 136 being pulled proximally, thereby further distally expanding the linkages 136 distal of the fixed pivot point 135 and thus causing the compaction tube 105 to travel distally and automatically tamp the sealing plug 110 into place in the incision 101, against the exterior surface of the artery or tissue wall 126. FIG. 5 shows one embodiment of the disclosure, wherein the linkages 136 have expanded such that the distal end of the compaction tube 105 has tamped the sealing plug 110 into place. Once the suture knot on the proximal end of the sealing plug 110 is secured, as the suture 102 has been pulled proximally, the suture 102 in the handle 118 can be released, and the excess suture 102 trimmed away. FIG. 6 provides a view showing the linkages 136 partially expanded, causing the linkages distal of the fixed pivot point 135 to expand distally, urging the compaction tube 105 distally toward the anchor 106 and sealing plug 110.

Figure 8:
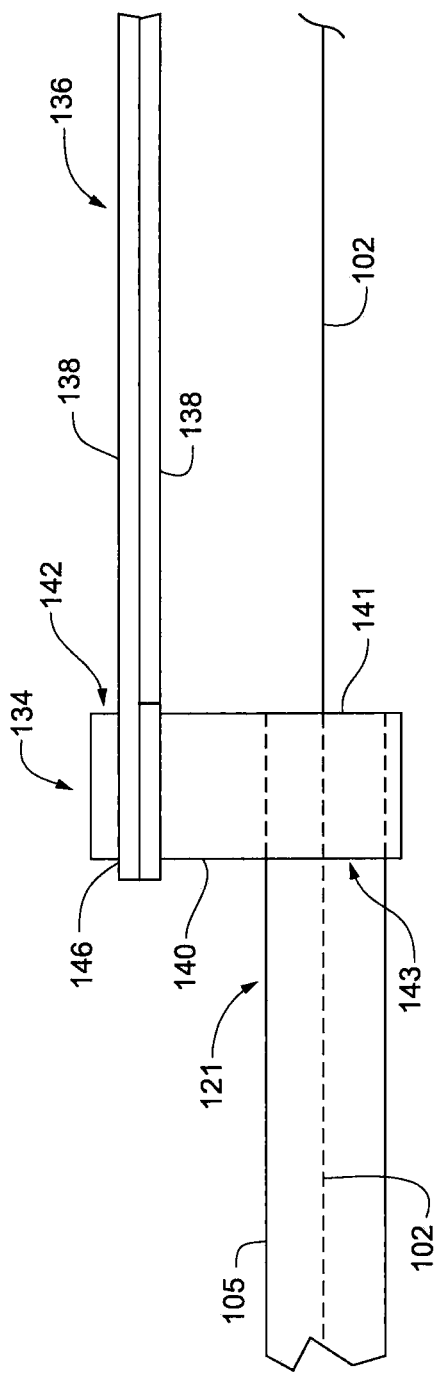
FIG. 8 is a side view of a pivot point fixture coupling a compaction member to a linkage.

The distal-most linkage 136 can be coupled to a proximate portion of the compaction tube 105 using various methods and fixtures. In one embodiment, as shown in FIG. 8, the distal-most pivot point 134 can include a portion of each of the two distal arms 138 of the linkage 136 and a portion of the compaction tube 105. The pivot point fixture 140 can be coupled to the linkage 136, for example, by being press fit into an aperture 146 in the distal end portion of each of the distal arms 138. The distal end portions of the distal arms 138 can overlap one another, such that the apertures 146 in the two distal arm 138 end portions are substantially aligned. The top portion 142 of the pivot point fixture 140 can be press fit through the two aligned apertures 146. The lower or bottom portion 143 of the pivot point fixture 140 can include an aperture 141 therethrough. The proximate end portion 121 of the compaction tube 105 can be press fit through the aperture 141 in the lower portion 143 of the pivot point fixture 140. Thus, the distal-most linkage 136 can be coupled to the proximate end portion 121 of the compaction tube 105 by way of the pivot point fixture 140. The pivot point fixture 140 can be a pin, peg, cylinder stub, or the like.

Figure 9:
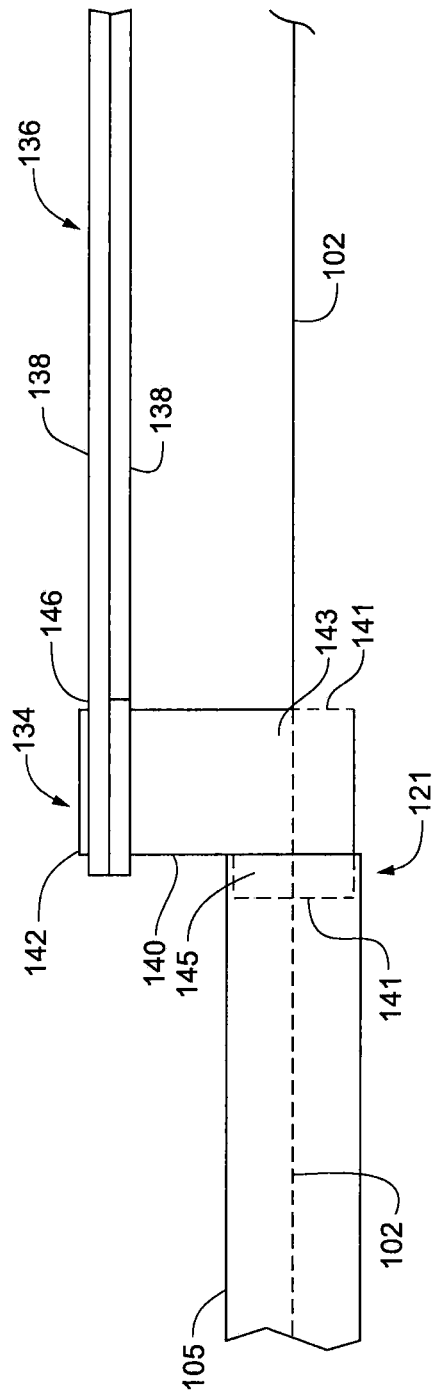
FIG. 9 is a side view of a pivot point fixture coupling a compaction member to a linkage.

Referring now to FIG. 9, there is shown another embodiment of the coupled compaction tube 105 and distal-most linkage 136. As noted above and also shown in FIG. 8, the pivot point fixture 140 can be coupled to the linkage 136, for example, by being press fit into an aperture 146 in the distal end portion of each of the distal arms 138. The distal end portions of the distal arms 138 can overlap one another, such that the apertures 146 in the two distal arm 138 end portions are substantially aligned, and the top portion 142 of the pivot point fixture 140 can be press fit through the two aligned apertures 146. The lower or bottom portion 143 of the pivot point fixture 140 can include an elbow 145 wherein the elbow 145 can be fitted snugly within the proximate end 121 of the compaction tube 105. The elbow 145 has an aperture 141 therethrough, such that the suture 102 can pass through the compaction tube 105 and the elbow 145 fitted within the compaction tube 105. Thus, the distal-most linkage 136 can be coupled to the proximate end portion 121 of the compaction tube 105 by way of the pivot point fixture 140. Other such pivot point fixtures 140 are contemplated, wherein the suture 102 can pass through the compaction tube 105 as well as through the lower portion 143 of the pivot point fixture 140. For example, the pivot point fixture 140 can be press fit through the two aligned apertures 146 in the two distal arm 138 end portions, and the lower or bottom portion 143 of the pivot point fixture can fit through an aperture in the surface of the compaction tube 105 and the bottom edge of the pivot point fixture 140 can unfold or expand once aligned adjacent the interior wall of the compaction tube and thus couple the compaction tube 105 to the linkage 136. Alternatively, a fastener can be disposed through the two aligned apertures 146 in the two distal arm 138 end portions, and the lower or bottom portion of the fastener can fit through an aperture in the surface of the compaction tube 105 and the bottom portion of the fastener can expand, for example, as a toggle bolt expands, once aligned adjacent the interior wall of the compaction tube and thus couple the compaction tube 105 to the linkage 136.

In another embodiment of a tissue puncture closure tool 300, as shown in FIG. 10, a single linkage 136 can be the driver of the compaction tube 105. Where components are similar to components of the tissue puncture closure device 100, 200 described above, similar numeric identifiers will be used. The tissue puncture closure device 300 includes a proximal end 103 and a second or distal end 119. A carrier tube 104 extends substantially from the proximal end 103 to the distal end 119 and includes an outlet at the distal end of the tube 104. As noted above, the carrier tube 104 is designed for insertion through a sheath 124 which, in turn, is designed for insertion through a percutaneous incision in a tissue layer and into a lumen. The distal end 107 portion of the carrier tube 104 houses a sealing plug 110. A bypass tube 108 envelops the distal end 107 of the carrier tube 104, and holds the anchor 106 in place in the bypass tube 108, distal of the end of the carrier tube 104. The bypass tube 108 (FIG. 10) includes an oversized head 115 that prevents the bypass tube 108 from passing through an internal passage of an insertion sheath 124. The anchor 106 can be an elongated, stiff, low-profile member preferably made of a biologically resorbable polymer. Similarly, the sealing plug 110 can be formed of a compressible sponge, pad, or foam, made of a hemostatic biologically resorbable material such as collagen, and can be configured in any shape so as to seal a tissue puncture.

The sealing plug 110 and anchor 106 are connected to one another by two sutures, threads, or filaments 102 that are also biologically resorbable. The sutures 102 extend distally from the linkage 136 in the handle 118 of the closure tool 300, through the carrier tube 104. The sutures 102 can be threaded through the sealing plug 110, then through an aperture in the anchor 106 and proximally back through the carrier tube 104 to the sealing plug 110. The sutures 102 are preferably threaded through a perforation or series of perforations in the sealing plug 110. The sutures 102 can also be threaded to form a slip-type knot at the proximal side of the sealing plug 110. The sutures 102 thus can connect the anchor 106 and the sealing plug 110 in a pulley-like arrangement that serves to cinch the anchor 106 and the sealing plug 110 together when the carrier tube 104 is pulled away from the anchor 106 and the sealing plug 110, sandwiching and locking the anchor 106 and sealing plug 110 together and thereby sealing a tissue puncture 101.

At the proximate end 103 of the tissue puncture closure tool 300, a compaction mechanism 132 is coupled to the handle housing 120. The compaction mechanism 132 comprises at least one linkage 136 wherein the linkage 136 further comprises four arms 138 and pivot points 134 connecting the arms 138. The compaction mechanism 132 also includes a plurality of spool or roller guides 122 or the like. The proximate-most pivot point 148 of the linkage 136 is coupled to the proximate end portion 121 of the tamping member 105 by way of a pivot point fixture 140. The pivot point fixture 140 can be a fixture as described in FIG. 8, FIG. 9, or any such similar fixture or fastener. The distal-most pivot point 149 of the linkage 136 can form a fixed pivot point 135, and can be coupled to the handle housing 120; to a top surface, bottom surface or side surface of the handle housing 120 such that a compaction tube 105 can pass above, below, or to the side of the fixed pivot point 135, and the compaction tube 105 can pass distally in the carrier tube 104. Thus, a portion of the compaction tube 105 is disposed within the handle 118 and a portion of the compaction tube 105 is disposed within the carrier tube 104. The distal-most pivot point 149 can be coupled to the handle housing 120 by, for example, a fastener that extends from the distal-most pivot point 149 to a handle housing 120 surface, or for example, by way of a molded portion of the handle housing 120 extending through the distal-most pivot point 149.

As noted above, the compaction mechanism 132 includes a plurality of spool or roller guides 122, or the like. The term "spool" will be used in the application to signify a spool, spindle, roller guide or other such similar device. As shown in FIGS. 10-13 there are four spool guides 122 as part of the compaction mechanism 132. Two spool guides 122 are disposed to each side of the compaction tube 105, in the distal end portion of the handle 118. The first spools 123 are disposed adjacent the compaction tube 105, one spool 123 disposed adjacent to one side of the compaction tube 105 and another spool 123 adjacent the opposite side of the compaction tube 105. The two first spools 123 are coupled to the handle housing 120, such that the spools 123 can serve as guides for a suture 102. Two additional spools 122 are disposed to the outside of the distal spools 123, or further away from the compaction tube 105, one second spool 125 disposed on one side of the compaction tube 105, and one second spool 125 disposed on the opposite side of the compaction tube 105. The second spools 125 can be disposed horizontally parallel to the first spools 123 or, alternatively, can be disposed proximate of the first spools 123. However, in another embodiment, there can be only two spools 123, disposed as described above. In yet another embodiment, there can be additional spools beyond the first 123 and second spools 125, arranged in the handle 118 and coupled to the handle housing 120, such that the compaction tube 105 can travel distally and through the carrier tube 104. The spools 122 can also be molded as a portion of the handle housing 120.

Sutures 102 can be attached to each side of the linkage 136; to the pivot points 134 positioned along a substantially horizontal axis, on opposite sides of the compaction tube 105. One suture 102 can be coupled to one pivot point 131 to one side of the compaction tube 105 and another suture 102 can be coupled to a second pivot point 133 on the opposite side of the compaction tube 105. The sutures then can travel distally, each around the at least one spool 123 on its respective side of the compaction tube 105, and then each passes through its respective aperture 150 in the compaction tube 105. In one embodiment, one suture can travel along second spool 125 and then along first spool 123, the spools guiding the suture 102, and then the suture 102 can pass through an aperture 150 in the compaction tube 105. A second suture 102 on the opposite side of the compaction tube 105 similarly can travel along second spool 125 and then along first spool 123, the spools guiding the suture 102, and then the suture 102 can pass through an aperture 150 in the compaction tube 105. The two sutures 102 then can travel distally through the compaction tube 105, through the sealing plug 110, through an aperture in the anchor 106, and then back proximally through the sealing plug, where the sutures 102 can form a slip-type knot at the proximate side of the sealing plug 110.

Here, as above, the compaction tube 105 can be an elongated tubular member that can be rigid or flexible and formed of any suitable material. The sutures 102 extend through the compaction tube 105 but are not directly connected thereto. Accordingly, the sutures 102 and compaction tube 105 are free to slide past one another. One end of one suture 102 is coupled to a pivot point 131, one end of a second suture 102 is coupled to another pivot point 133, and the other end of the sutures 102 form a slip-type knot at the proximate end of the sealing plug 110. Further, when distal tension is applied to the sutures 102, the pivot points 131, 133, are pulled distally and outwardly-horizontally, thereby the arms 138 are pulled in a distal direction and out horizontally, such that the longitudinal axis of the linkage 136 is shortened and the horizontal axis of the linkage 136 is lengthened. The distal-most pivot point 149 of the linkage 136 is a fixed pivot point coupled to the handle housing 120, however the proximate-most pivot point 148 is coupled to the proximate end portion 121 of the compaction tube 105 and is free to travel distally in the handle 118, toward the anchor 106 and sealing plug 110.

Figure 11:
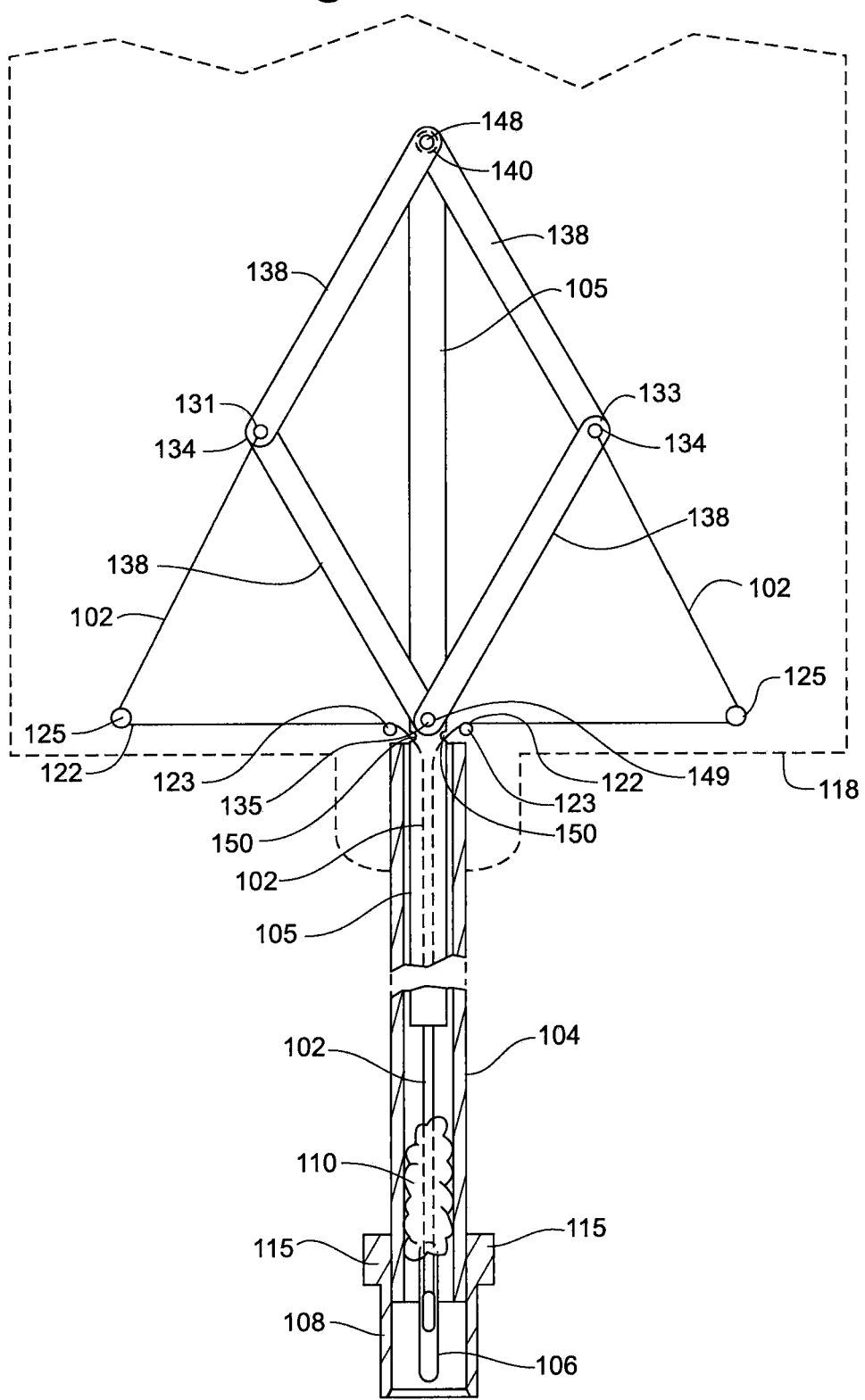
FIG. 11 is a close-up of the compaction mechanism of the tissue puncture closure tool of FIG. 10.

Referring to FIG. 11, there is shown an enlarged image of the compaction mechanism 132 at "rest", prior to the tissue puncture closure tool 300 being inserted into a sheath 124. Thus, the by-pass tube 108 with the over-sized head 115 is still disposed at the distal end of the closure tool 300. Spools 123, 125 are coupled to the handle housing 120, as is the proximate-most pivot point 148. In operation, the tissue puncture closure tool 300 can be inserted into a sheath 124 that has already been inserted into a puncture tract 101. The bypass tube 108, which holds the anchor 106 in place at the distal end of the carrier tube 104, bears against a surface of the sheath 124. The bypass tube 108 (FIG. 11) includes an oversized head 115 that prevents the bypass tube 108 from passing through an internal passage of the insertion sheath 124. Therefore, as the puncture closure tool 300 is inserted into the insertion sheath 124, the oversized head 115 bears against a surface of the insertion sheath 124. Further insertion of the puncture closure tool 300 results in sliding movement between the carrier tube 104 and the bypass tube 108, releasing the anchor 106 from the bypass tube 108. However, the anchor 106 remains in the flush arrangement shown in FIG. 11 following release from the bypass tube 108 as the insertion sheath 124 continues to limit anchor 106 movement.

The insertion sheath 124 includes a monofold at a second or distal end of the insertion sheath 124. The monofold acts as a one-way valve to the anchor 106. The monofold is a plastic deformation in a portion of the insertion sheath 124 that elastically flexes as the anchor 106 is pushed out through the distal end of the sheath 124. Typically, after the anchor 106 passes through the distal end of the insertion sheath 124 and enters the artery lumen 116, the anchor 106 is no longer constrained to the flush arrangement with respect to the carrier tube 104 and the anchor 106 deploys, can catch on the distal end of the insertion sheath 124, and rotates to the position shown in, for example, FIG. 12.

The closure tool 300 can begin to be retracted, which can further position the anchor 106 in proper position against the inner tissue wall, for example, against the inner wall 111 of the artery. When resistance to further retraction of the closure tool 300 is felt by an operator, the closure tool 300 and the insertion sheath 124 can be withdrawn together, causing the anchor 106 to anchor itself within the artery 114 against the artery wall 111. With the anchor 106 anchored within the artery 114 at the puncture site 117, further retraction of the closure tool 300 and insertion sheath 124 causes the sealing plug 110 to deploy from the distal end 107 of the carrier tube 104, thereby depositing the plug 110 within the incision or puncture tract 101. In addition, as the tissue puncture closure tool 300 and sheath 124 are withdrawn, tension on the sutures 102 increases such that the horizontal pivot points 131, 133 of the linkage 136 are pulled distally and outwardly, and the horizontal axis of the linkage 136 is lengthened. Further, as the horizontal axis is lengthened, the vertical or longitudinal axis of the linkage 136 is shortened, and the proximate-most pivot point 148 travels distally along the vertical axis towards the distal-most pivot point 149. The proximate-most pivot point 148 is coupled to the compaction tube 105, thus as the proximate-most pivot point 148 travels towards the distal-most pivot point 149, so does the compaction tube 105. Thus the compaction tube 105 travels distally through the carrier tube 104 and automatically tamps the sealing plug 110 against the anchor 106 and against the exterior wall 126 of the artery 114 or other tissue exterior wall surface. The sealing plug 110 is tamped while the carrier tube 104 is still arranged adjacent to the puncture 117 in the artery 114, reducing or eliminating any gaps that may otherwise occur between the sealing plug 110 and the puncture 117 in the artery 114. Tension on the sutures 102 can pull the slip-type knot on the proximal side of the sealing plug 110, thus tightening the knot against the sealing plug 110 and fixing the sealing plug 110 in place in the incision tract 101, sandwiching the artery wall 111 between the anchor 106 and sealing plug 110. Once the suture 102 knot on the proximal side of the sealing plug 110 is secure, the sutures 102 in the handle 118 can be released, and the excess sutures 102 trimmed away. For example, a hemostat can be used to push down or depress the skin that is located around the suture, and the suture can be cut using a scalpel or razor.

Figure 12:
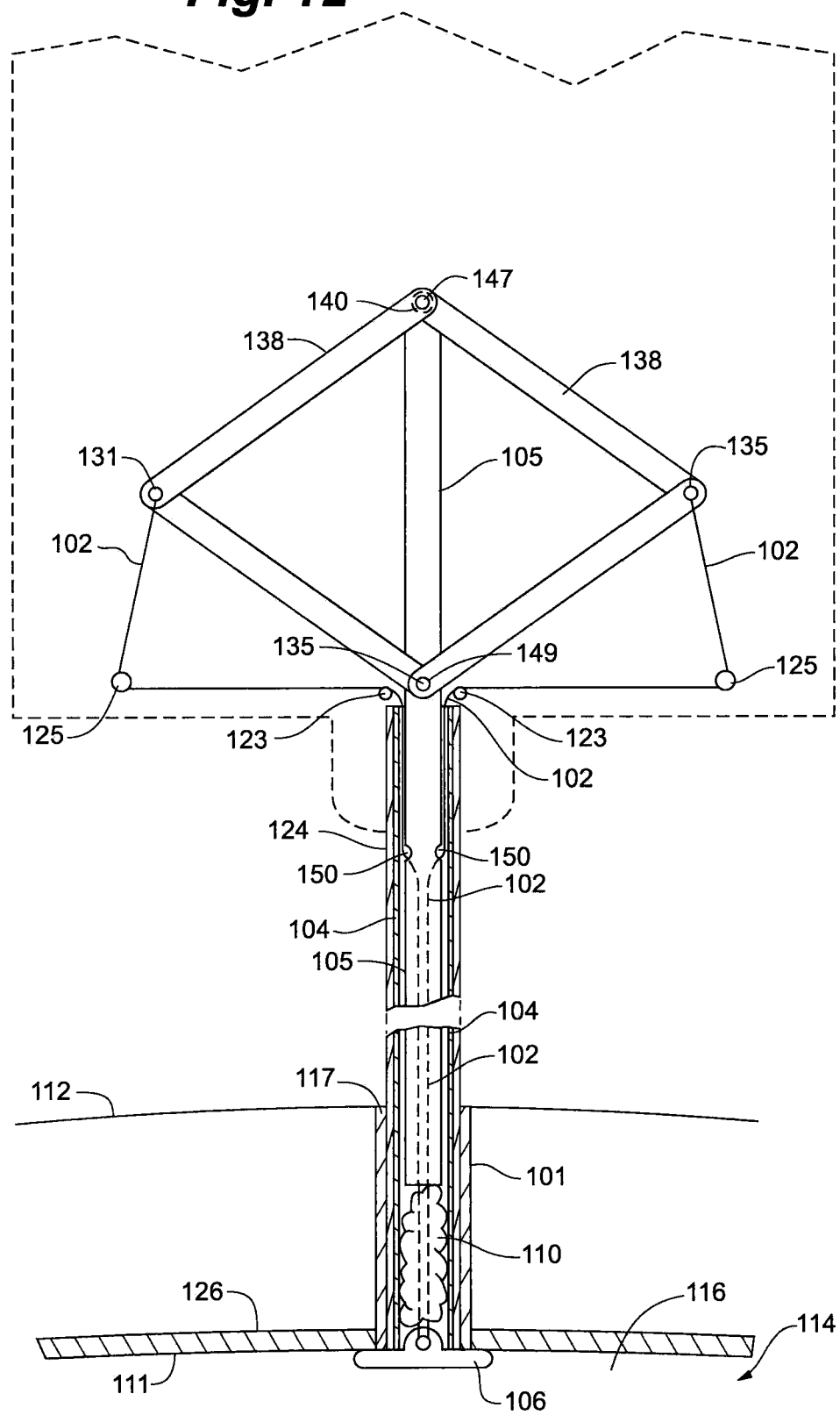
FIG. 12 is a top view of the tissue puncture closure tool of FIG. 10, with the compaction mechanism somewhat extended.
Figure 13:
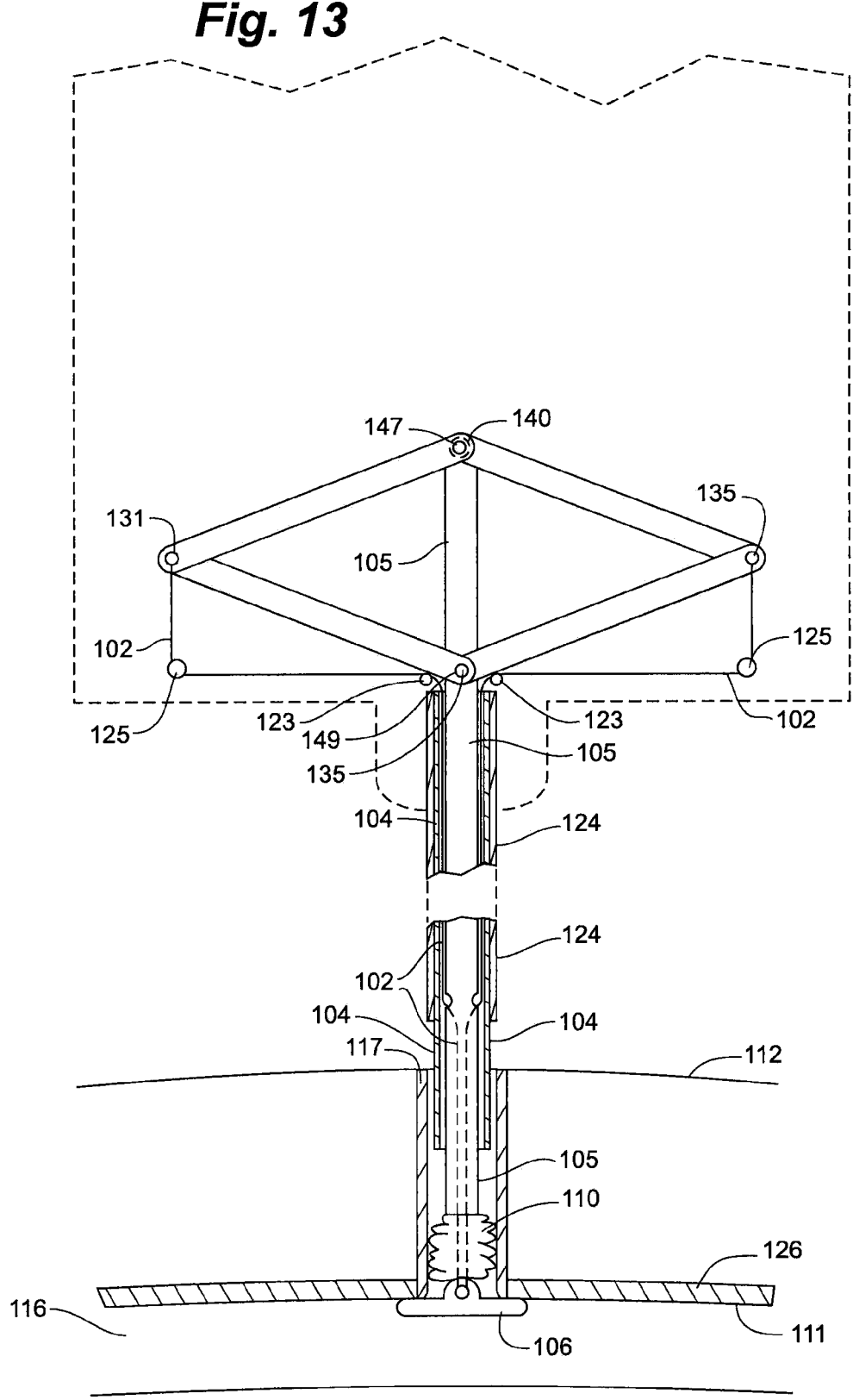
FIG. 13 is a top view of the tissue puncture closure tool of FIG. 10 with the compaction mechanism substantially extended and the sealing plug deployed and compacted.

FIG. 12 provides a view showing the linkage 136 collapsing horizontally, with the horizontal axis of the linkage 136 lengthening and the vertical axis of the linkage 136 shortening. This movement, in turn, urges the compaction tube 105 distally toward the anchor 106 and sealing plug 110. The sealing plug 110 is ejected from the distal end of the carrier tube 104 and is disposed within the puncture tract 101. As the carrier tube 104 and sheath 124 are withdrawn further, the linkage 136 collapses further, with the compaction tube 105 tamping the sealing plug 110 into place, as shown in FIG. 13. In addition, by placing tension on or pulling the sutures 102 away proximally from the puncture tract 101, the sutures 102 cinch and lock (with a slip knot or the like) together the anchor 106 and the sealing plug 110, sandwiching the artery wall 111 between the anchor 106 and sealing plug 110. The force exerted by the compaction tube 105 and the cinching together of the anchor 106 and sealing plug 110 by the sutures 102 can also cause the sealing plug 110 to deform radially outward within the puncture tract and function as an anchor on the proximal side of the artery wall 111. Once the sealing plug 110 is securely disposed in the puncture tract 101, the carrier tube 104 and sheath 124 can be withdrawn from the tissue tract 101 and the sutures 102 can be cut.

The preceding description has been presented only to illustrate and describe exemplary embodiments of disclosure. It is not intended to be exhaustive or to limit the disclosure to any precise form disclosed. Many modifications and variations are possible in light of the above teaching. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the disclosure be defined by the attached claims and their legal equivalents.

What is claimed is:

1. A tissue puncture closure device comprising:
    a handle disposed at a first end of the closure device, the handle including a handle housing;
    a filament, a first end extending from the first end at the handle to a second end;
    a carrier tube extending from the handle;
    a sealing plug assembly disposed in the carrier tube and coupled to a second end of the filament; and
    an automatic compaction mechanism, wherein a proximal end of the automatic compaction mechanism is coupled to the handle housing and the automatic compaction mechanism extends through the carrier tube, the automatic compaction mechanism comprising at least one linkage, wherein the at least one linkage comprises a plurality of arms and the arms are interconnected by way of pivot points.

2. The tissue puncture closure device of claim 1, comprising a plurality of linkages.

3. The tissue puncture closure device of claim 2, wherein the linkages are interconnected in series by pivot points.

4. The tissue puncture closure device of claim 3, the automatic compaction mechanism further comprising a tamping member, the tamping member at least partially disposed within the carrier tube, a distal end of a distal-most linkage coupled to a proximal end of the tamping member.

5. The tissue puncture closure device of claim 4, wherein a proximal portion of the automatic compaction mechanism comprises a plurality of proximal linkages wherein one pivot point connecting two proximal linkages is also coupled to the handle housing.

6. The tissue puncture closure device of claim 5, further comprising a spool, wherein the spool is coupled to the handle housing proximate of the proximal end of the automatic compaction mechanism.

7. The tissue puncture closure device of claim 6, wherein the first end of the filament is coupled to a proximate-most pivot point of the proximate-most linkage of the automatic compaction mechanism and passes over the spool.

8. The tissue puncture closure device of claim 7, the sealing plug assembly comprising a sealing plug and an anchor wherein the second end of the filament is connected to the anchor and the sealing plug for slidably cinching the anchor and sealing plug together about a tissue puncture wherein the sealing plug is slidably disposed on the filament proximal to the anchor.

9. The tissue puncture closure device of claim 7, the linkages adapted to expand distally or longitudinally upon application of a tensioning force supplied by the filament upon retraction of the closure device, the tamping member coupled to the distal pivot point of the distal-most linkage and adapted to tamp the sealing plug towards the anchor.

10. A tissue puncture closure device comprising:
  a handle disposed at a first end of the closure device, the handle including a handle housing;
  a carrier tube extending from the handle;
  a sealing plug assembly disposed in the carrier tube;
  a tamping member slidingly disposed at least partially in the carrier tube and proximate of the sealing plug assembly; and
  an automatic compaction mechanism, wherein a proximal end of the automatic compaction mechanism is coupled to the tamping member, the automatic compaction mechanism comprising at least one linkage, the at least one linkage comprising a plurality of arms, and pairs of arms of the plurality of arms are interconnected by way of pivot points.

11. The tissue puncture closure device of claim 10, the distal-most end of the automatic compaction mechanism comprising a pivot point and coupled to the handle housing.

12. The tissue puncture closure device of claim 11, comprising one linkage comprising of four arms.

13. The tissue puncture closure device of claim 11, further comprising two filaments, each filament first end coupled to a respective pivot point of one linkage, the pivot points positioned substantially along a horizontal axis, the filaments passing along a plurality of rollers, and extending from the first end at the handle to a second end.

14. The tissue puncture closure device of claim 12, further comprising four spool guides, the spool guides disposed equally on either side of the tamping member, wherein the tamping member comprises a plurality of apertures, at least one aperture on each side of the tamping member, the apertures adapted to accommodate the two filaments.

15. The tissue puncture closure device of claim 14, a second end of each filament coupled to the sealing assembly, the sealing assembly comprising a sealing plug and an anchor.

16. The tissue puncture closure device of claim 15, wherein the second end of each filament is connected to the anchor and the sealing plug for slidably cinching the anchor and sealing plug together about a tissue puncture wherein the sealing plug is slidably disposed on the filaments proximal to the anchor.

17. The tissue puncture closure device of claim 16, the linkage adapted to expand horizontally upon application of a tensioning force supplied by the filaments upon retraction of the closure device, the tamping member coupled to the proximal pivot point of the proximal-most linkage and urged to slidingly pass distally through the carrier tube and tamp the sealing plug towards the anchor.

* * * * *